United States Patent [19]
Raffin et al.

[11] Patent Number: 4,686,100
[45] Date of Patent: Aug. 11, 1987

[54] METHOD FOR THE TREATMENT OF ADULT RESPIRATORY DISTRESS SYNDROME

[75] Inventors: Thomas A. Raffin; John H. Stevens, both of Palo Alto, Calif.

[73] Assignee: The Board of Trustees of the Leland Stanford Junior University, Stanford, Calif.

[21] Appl. No.: 718,918

[22] Filed: Apr. 2, 1985

[51] Int. Cl.$^4$ ............................................. A61K 39/00
[52] U.S. Cl. .................................... 424/85; 424/101; 530/387; 514/921
[58] Field of Search ......................... 424/85; 530/387; 436/821

[56] References Cited

PUBLICATIONS

Kraut et al, "Effects of CVF Treatment on Latent FeLV Infection", *J. Virology*, vol. 54(3), 1985, pp. 873-875.
Yancy et al, "Human C5a Modulates Moacytes Fe and C3 Receptor Expression", *J. Immunol.*, vol. 135(1), 1985, pp. 465-470.
C.A. #176799b, vol. 103, 1986, Johnson et al.
C.A. #86170k, vol. 103, 1986, Lanier et al.
Craddock, P. R., et al., "Complement (C5a)-Induced Granulocyte Aggregation in Vitro: A Possible Mechanism of Complement-Mediated Leukostasis and Leukopenia," J. Clin. Invest. 60, 260-264 (Jul. 1977).
Duff, Patrick, "Pathophysiology and Management of Septic Shock," J. Reprod. Med. 24 (3), 109-117. (Mar. 1980).
Fein, A. M., et al., "The Risk Factors, Incidence, and Prognosis of ARDS following Septicemia," Chest 83 (1), 40-42 (Jan. 1983).
Fowler, A. A., et al., "Adult Respiratory Distress Syndrome: Risk with Common Predispositions," Ann. Int. Med. 98 (5), 593-597 (May 1983).
Gelfand, J. A., et al., "Alternative Complement Pathway Activation Increases Mortality in Model of Burn Injury in Mice," J. Clin. Invest. 70, 1170-1176 (Dec. 1982).
Hammerschmidt, D. E., et al., "Corticosteroids Inhibit Complement-Induced Granulocyte Aggregation: A Possible Mechanism for Their Efficacy in Shock States," J. Clin. Invest. 63, 798-803 (Apr. 1979).
Hammerschmidt, D. E., et al., "Association of Complement Activation and Elevated Plasma-C5a with Adult Respiratory Distress Syndrome," The Lancet, 947-949 (May 3, 1980).
Hammerschmidt, D. E., et al., "Granulocyte Aggregometry: A Sensitive Technique for the Detection of C5a and Complement Activation," Blood 55 (6), 898-902 (Jun. 1980).
Hosea, Steven, et al., "Role of Complement Activation in a Model of Adult Respiratory Distress Syndrome," J. Clin. Invest. 66, 375-382 (Aug. 1980).
Parrish, D. A., et al., "Pulmonary Response of Fifth Component of Complement-Sufficient and -Deficient Mice to Hyperoxia," J. Clin. Invest. 74, 956-965 (Sep. 1984).
Rinaldo, J. E. and Rogers, R. M., "Adult Respiratory Distress Syndrome," New England J. Med. 306, 900-909 (Apr. 15, 1982).
Sacks, Thomas, et al., "Oxygen Radicals Mediate Endothelial Cell Damage by Complement-Stimulated Granulocytes: An In Vitro Model of Immune Vascular Damage," J. Clin. Invest. 61, 1161-1167 (1977).
Stevens, J. H. and Raffin, T. A., "Adult Respiratory Distress Syndrome—I. Aetiology and Mechanisms," Post. Med. J. 60, 505-513 (Aug. 1984).
Stevens, J. H. and Raffin, T. A., "Adult Respiratory Distress Syndrome—II. Management," Post. Med. J. 60, 573-576 (Sep. 1984).
Tate, R. M. and Repine, J. E., "Neutrophils and the Adult Respiratory Distress Syndrome," Am. Rev. Respir. Dis. 128 (3), 552-559 (Sep. 1983).
Tonnesen, M. G., et al., "Neutrophil-Endothelial Cell Interactions: Modulation of Neutrophil Adhesiveness Induced by Complement Fragments C5a and C5a des arg and Formyl-Methionyl-Leucyl-Phenylalanine in Vitro," J. Clin. Invest. 74, 1581-1592 (Nov. 1984).
Weinberg, P. F., "Biologically Active Products of Complement and Acute Lung Injury in Patients with the Sepsis Syndrome," Am. Rev. Respir. Dis. 130, 791-796 (1984).

Primary Examiner—Morton Foelak
Assistant Examiner—Garnette D. Draper
Attorney, Agent, or Firm—Ciotti & Murashige

[57] ABSTRACT

A method for treating adult respiratory distress syndrome (ARDS) and sepsis in a patient in need thereof which comprises administering to said patient an antibody to complement component C5a or the des Arg derivative thereof in an amount effective to treat ARDS and sepsis.

8 Claims, No Drawings

METHOD FOR THE TREATMENT OF ADULT RESPIRATORY DISTRESS SYNDROME

FIELD OF INVENTION

This invention is directed to a novel method for the treatment of adult respiratory distress syndrome (ARDS) and sepsis.

BACKGROUND OF INVENTION

The adult respiratory distress syndrome (ARDS) is a common and often fatal complication of septic shock (see Fowler, A. A., et al. (1983), "Adult respiratory distress syndrome: Risk with common predispositions." Ann. Int. Med. 98, 593-597, and Fein, A. M., et al. (1983), "The risk factors, incidence, and prognosis of ARDS following septicemia," Chest 83, 40-42). Several cellular and humoral factors have been implicated in the pathogenesis of ARDS, including neutrophils, platelets, fibrin, arachidonic acid metabolites, serotonin, histamine and C5a (see Stevens, J. H. and T. A. Raffin (1984), "Adult respiratory distress syndrome—I. Etiology and mechanisms." Post. Med. J. 60, 505-513). Recent reports have suggested that C5a mediates neutrophil attraction, aggregation, activation and subsequent pulmonary endothelial damage thus being a critical component in the pathogenesis of ARDS (see Tate, R. M. and J. E. Repine (1983), "Neutrophils and the adult respiratory distress syndrome: State of the art." Am. Rev. Resp. Dis. 128, 802-806; Sacks, T., et al. (1978), "Oxygen radicals mediate endothelial cell damage by complement stimulated granulocytes. An in vitro model of immune vascular damage." J. Clin. Invest. 61, 1161-1167; and Craddock, P. R., et al. (1977), "Complement (C5a)-induced granulocyte aggregation in vitro: A possible mechanism of complement-induced leukostastis and leukopenia." J. Clin. Invest. 60, 260-264). This sequence of events may be the primary pathogenetic mechanism for the development of ARDS in septic shock (see Stevens, J. H. and T. A. Raffin (1984), "Adult respiratory distress syndrome—I. Etiology and mechanisms." Post. Med. J. 60, 505-513). In vitro studies have demonstrated that C5a generated from endotoxin or zymosan-activated plasma causes neutrophil aggregation (see Hammerschmidt, D. E., et al. (1980), "Granulocyte aggregometry: A sensitive technique for the detection of C5a and complement activation." Blood 55, 898-902). In addition, C5a-activated neutrophils are more adherent and are cytopathic to endothelial cells in tissue culture (see Tonnesen, M. G., et al. (1984), "Neutrophil-endothelial cell interactions: Modulation of neutrophil adhesiveness induced by complement fragments C5a and C5a des Arg and formyl-methionyl-leucyl-phenylanaline in vitro. J. Clin. Invest. 74, 1581-1592).

In vivo studies investigating mice which are genetically deficient in C5 have established that C5 is required for pulmonary edema formation in response to pneumococcal sepsis, scald wounds and hyperoxia (see Hosea, S. F., et al. (1980), "Role of complement activation in a model of adult respiratory distress syndrome." J. Clin. Invest. 66, 375-382; Gelfand, J. A., et al. (1982), "Alternative complement pathway activation increases mortality in a model of burn injury in mice." J. Clin. Invest. 70, 1170-1176; and Parrish, D. A., et al. (1984), "Pulmonary response of fifth component of complement-sufficient and-deficient mice to hyperoxia." J. Clin. Invest. 74, 956-965). When patients at high risk to develop ARDS were followed prospectively, detection of an elevated C5a was a useful predictor of the onset of ARDS (see Hammerschmidt, D. E., et al. (1980), "Association of complement activation and elevated plasma-C5a with adult respiratory distress syndrome: Pathophysiological relevance and possible prognostic value." Lancet 1, 947-949). A prospective study of 40 patients with sepsis (P. S. Weinberg, et al. (1984), Am. Rev. Respir. Dis. 130, 791-796) found levels of C5a des Arg and C3a des Arg were elevated in nearly all of the patients. Also within this patient population 60% had severe lung injury and 25% had ARDS.

The present invention provides a novel means of treating ARDS and sepsis which comprises administration of antibody to complement factor C5a.

SUMMARY OF THE INVENTION

The present invention is a method for the treatment of adult respiratory distress syndrome (ARDS) in a patient in need thereof which comprises administering to said patient an antibody to complement component C5a or the des Arg derivative thereof. The present invention also providew a method for the treatment of sepsis or alleviating the symptoms of sepsis in a patient in need thereof which comprises administering to said patient an antibody to complement component C5a or C5a des Arg. The antibody employed in the present invention may be a polyclonal antibody or monoclonal antibody.

DETAILED DESCRIPTION OF INVENTION

ARDS may be characterized as acute respiratory failure due to noncardiogenic pulmonary edema which is often an aftereffect of shock, systemic sepsis, battlefield or highway trauma, viral respiratory infections and various other injuries or conditions (see Rinaldo, J. E. and and R. M. Rogers (1981), Adult Respiratory Distress Syndrome 306, 900-909). Current methods of ARDS therapy include intensive respiratory, cardiovascular and nutritional support. Mechanical ventilation with positive end-expiratory pressure is the standard method of respiratory management in patients with ARDS (see Stevens, J. H. and T. A. Raffin (1984), "Adult respiratory distress syndrome—II. Management." Postgr. Med. J. 60, 573-576). Corticosteroid therapy (see Hammerschmidt, et al. (1979), "Corticosteroids inhibit complement induced granulocyte aggregation." J. Clin. Invest. 63, 798-803), e.g., methylprednisolone or administration of cyclooxygenase inhibitors, e.g., prostaglandin E, have met with only limited benefit to the ARDS patient. The clinical manifestations of sepsis and current methods of treatment are set forth in J. Reprod. Med. 24, 109-117 (1980) by P. Duff.

The method of the present invention will be most beneficial to the ARDS or sepsis patient if implemented at the very early onset of conditions to be treated or even more preferably prior to any overt symptoms of sepsis or ARDS. Early onset of ARDS may be monitored by use of an immunoassay for C5a or C5a des Arg. The method of the present invention preferably will be used in combination with other therapeutic means. The method of the present invention attenuates ARDS and thus markedly reduces the symptoms of ARDS; but nevertheless, it is anticipated that respiratory cardiovascular and nutritional support will be provided the patient as needed. Additionally the method of the present invention may be combined with other pharmacological means for the treatment of ARDS and sepsis.

The method of the present invention can be used to treat any warm blooded animal having ARDS or sepsis which results from or is associated with the activation of complement giving rise to C5a or the des Arg derivative thereof. The preferred embodiment of this invention is the treatment of humans having ARDS. Another preferred embodiment of the present invention is the treatment of humans having sepsis. Preferably anti-human C5a des Arg is administered in an amount of from about 1 to about 100 mg/kg of body weight per day for one to 3 days with the dosage being diminished from day one to day 3 of treatment. For example, 2 to 5 grams of antibody would be administered on the first day, one to 3 grams on the second day, with 0.5 to 2 grams being administered on the third day. Of course whether fewer days or more days of treatment are needed will depend on the condition of the patient at the time therapy is initiated and the response of the patient to the therapy. The antibody is infused generally by an intravenous drip. Although anti-human C5a des Arg is the preferred antibody in practicing the present invention, antibody to any warm blooded species of C5a or C5a des Arg which cross-reacts sufficiently with human C5a or C5a des Arg may be employed.

Complement component C5a is a polypeptide which is inactivated in-vivo by a serum carboxypeptidase to complement C5a des Arg, inactivation occurring only after all available white blood cell binding sites for C5a have been saturated. (Hugli, T. E. and H. J. Muller-Eberhard (1978), "Anaphylatoxins: C3a and C5a." Adv. Immunol. 26, 1–53.) In raising a complement C5a antibody thus, it is generally C5a des Arg which is employed. Although C5a des Arg is physiologically inactive it is immunogenic and antibody to C5a des Arg will cross-react in vivo with C5a as well as C5a des Arg. The antibody is raised by standard procedures by injecting C5a des Arg from one species into an animal of a different species. For example human C5a des Arg may be injected into, e.g., rabbits, goats, sheep, or horses to raise anti-human C5a des Arg. Monoclonal antibody to C5a or C5a des Arg is produced by means well known in the art using either C5a or C5a des Arg isolated from a suitable warm blooded animal or humans or chemically synthesized C5a or C5a des Arg.

The following experiments further illustrate the invention.

ANTI-C5a des Arg PREPARATION

Immunogen was prepared from zymosan-activated human plasma and gefiltration/ion exchange chromatography according to the method described by Hugli and Chenoweth (Hugli, T. E. and D. E. Chenoweth (1980), "Biologically active peptides of complement: Techniques and significance of C3a and C5a measurements." In Laboratory and Research Methods in Biology and Medicine, R. M. Nakamura, W. R. Ditto, E. S. Tucker III, eds., Alan R. Liss, Inc., New York, N.Y., 443–460). The C5a des Arg obtained was checked for its purity with cellulose acetate electrophoresis and amino acid analysis and used as the immunogen. New Zealand white rabbits were immunized with the immunogen, and antiserum to human complement C5a des Arg was obtained. Anti-human C5a des Arg has complete cross-reactivity with human C5a (Hugli, T. E., et al. (1981), "Isolation of three separate anaphylatoxins from complement-activated human serum, "Molec. Cell Biochem. 41, 59–66).

Rabbit anti-human C5a des Arg was titrated by radioimmunoassay (Upjohn Diagnostics, The Upjohn Company, Kalamazoo, MI). The titer of the antiserum (% bound label/total label) used in this experiment was 1:1200.

Immunoglobulin was prepared from 10 ml of the antiserum with a modified method for horse IgG preparation (Wechter, W. J., et al. (1979), "Manufacture of anti-thymocyte globulin (ATGAM) for clinical trials," Transplantation 28, 303–307). The final solution of IgG fraction from the antiserum was made particle-free by centrifugation at 18,000 rpm for 30 minutes. Concentration of protein was determined with an ultraviolet absorption at 280 nm (E 280 nm, 1 mg/ml=1.5). Non-specific immunoglobulin from non-immunized New Zealand white rabbits was prepared as above and was used as sham antibody infusion for animals in groups I and II.

LEUKOCYTE AGGREGATION

Anticoagulated (10 U heparin/ml blood) venous blood from Macaca fascicularis primates was used and neutrophils were obtained using a modified method of Craddock, et al., ibid. Our modification utilized phosphate buffered saline with 9% glucose (PBSG) rather than Hanks balanced salt solution with albumin.

Plasma was prepared by incubating 0.4 ml of plasma with 20 $\mu$l of 2 mg/ml endotoxin (E. coli J96) at 37° C. for 30 minutes and at 56° C. for 30 minutes. Plasma was rendered particulate free by centrifuging at 5000 g for 10 minutes after the incubation with endotoxin. Aggregation of neutrophils was determined by aggregometry of neutrophils ($5 \times 10^6$ cells/ml of PBSG) in an aggregometer (PAP 4, bio/Data Corp., Willow Grove, PA). The stimuli for aggregation were: (a) endotoxin activated plasma; (b) endotoxin activated plasma incubated for 15 minutes with non-specific rabbit IgG; and (c) endotoxin activated plasma incubated for 15 minutes with anti-C5a des Arg IgG. Aggregation was induced by adding 20 $\mu$l of each respective stimulus to 250 $\mu$l of neutrophil suspension.

ANIMAL PREPARATION

Twelve adult male Macaca fascicularis primates (cynomolgus) were used in the study weighing 4.8–7.2 kg (Table I). They were initially anesthetized with 20 mg/kg of methohexital and 5 mg/kg of succinylcholine and maintained with 5 mg/kg/hr of pentobarbitol and 0.1 mg/kg/hr of pancuronium (Harvard infusion pump), and placed supine on a heating pad. The animals were intubated and ventilated with room air (Health Dyne, Model 121, Marietta, GA) using a tidal volume of 15 mg/kg and a respiratory rate adjusted to maintain a $PaCO_2$ of 35±3 mmHg.

A 4F arterial line was inserted through a femoral artery into the abdominal aorta to measure arterial pressures and sample arterial blood gases. A 5F thermal dilution Swan-Ganz catheter was inserted through a femoral vein to the pulmonary artery in order to measure pulmonary arterial and wedge pressures and to monitor cardiac output (Edwards Model 9520A Thermodilution Cardiac Output Computer and Catheters, Santa Ana, CA). Position of the catheters was confirmed by pressure recordings on a 4-channel strip chart recorder (Hewlett Packard, Model 81064A, Palo Alto, CA). A central venous line was inserted through the opposite femoral vein for administration of antibody. Precordial ECG leads were placed for evaluation of heart rate and rhythm.

PREPARATION OF BACTERIA

E. Coli. J96 (04:K6:H+), a human bacteremic-pyelonephritic isolate, is hemolytic, colicin V positive, resistant to the bactericidal action of normal serum, and simultaneously mannose and $\alpha$Gal 1T4 $\rightarrow \beta$Gal binding (Hull, R., et al. (1981), "Construction and expression of recombinant plasmids encoding Type 1 or D-Mannose-Resistant pili from a urinary tract infection. *Escherichia Coli* isolate." Infect. Immun. 33, 933–938). Stock cultures were stored in Luria broth with 10% glycerol at $-70°$ C. Stock cultures were innoculated onto trypicose soy agar (TSA) plates and incubated at 37° C. for 18 hours. The 18-hour TSA cultures were harvested into normal saline using sterile fiberfree dacron swabs. The number of colony forming units (CFU) per ml of normal saline was determined by construction of standard curves by comparing the optical density at 620 nm (1 cm light path) to the number of CFU of serially diluted cultures by the agar pour technique. The J96 CFU standard curves were reproducible as determined by identical curves on three different occasions that were each performed in triplicate. The stock intravenous bacteria innoculum was $2.0 \times 10^9$ bacteria per ml of saline. This innoculum represented a point on the CFU-optical density standard curve that was on the straight portion of the curve and was randomly checked and confirmed by culture techniques on four different occasions in duplicate during the course of the experiment.

EXPERIMENTAL PROTOCOL

Animals were separated into three experimental groups. Group I (n=4) were control animals to receive 5 mg pooled IgG from non-immunized rabbits (sham IgG) and 5 ml/kg of sterile saline as a mock *E. coli* infusion. Group II (n=4) were septic animals to receive 5 mg sham rabbit IgG and 5 ml/kg of the E. coli suspension ($1 \times 10^{10}$/kg). Group III (n=4) were septic animals to receive 5 mg of rabbit anti-human C5a des Arg and 5 ml/kg of the E. coli suspension.

Following the completion of line placement a pulmonary capillary wedge pressure (PCWP) was measured. If the PCWP<5 mmHg, fluid was administered according to a predetermined protocol to bring the PCWP to 5 mmHg. Throughout the experiment the fluid resuscitation protocol was used to maintain the PCWP at 5 mmHg.

The fluid resuscitation protocol consisted of normal saline (N/S) administered intravenously to maintain the PCWP at 5 mmHg. PCWP measurement was performed at a minimum interval of 0.2 hours. If the PCWP was <5 mmHg, 20 ml of N/S was administered over one minute. A PCWP measurement was performed immediately after completion of the bolus. If the PCWP was =5 mmHg no additional fluid was administered. If the PCWP was <5 mmHg 40 ml of N/S was administered over one minute and a PCWP measurement was performed. This sequence was repeated until the PCWP was =5 mmHg. The pulmonary artery diastolic (PAD) pressure was evaluated during the infusion of N/S. If the PAD had an increase >3 mmHg the fluid administration was stopped and a PCWP measurement performed. If the PCWP was <5 mmHg the fluid bolus was completed; if the PCWP was =5 mmHg no additional fluid was administered.

Baseline data was obtained when the PCWP was 5 mmHg. Data included heart rate; systolic, diastolic and mean arterial pressure (MAP); systolic, diastolic and mean pulmonary arterial pressure (PAP); pulmonary capillary wedge pressure (PCWP); central venous pressure; thermal dilution cardiac output; arterial blood gases; and circulating peripheral neutrophil number.

Immediately after baseline data was obtained antibody infusion was initiated. Five mg of sham or anti-C5a antibody was diluted in 40 ml N/S and one-third of the solution was infused as a bolus over one minute. The remaining antibody was infused over 20 minutes using a Harvard infusion pump.

In groups II and III, *E. coli* infusion ($1 \times 10^{10}$ *E. coli*/kg) was initiated 5 minutes after the initiation of the bolu antibody infusion and continued at a constant rate for 30 minutes using a Harvard infusion pump. The end of the *E. coli* infusion was designated time zero and the protocol was carried out for 4 hours. Animals that survived the 4 hour protocol were sacrificed at 4.2 hours.

Arterial blood samples were collected every hour anaerobically and $PO_2$, $PCO_2$, and pH were measured using a Corning blood gas analyzer (Corning, Model 178, Medfield, MA). The alveolar-to-arterial oxygen difference ($AaDO_2$) was calculated (assumed respiratory exchange ratio of 0.8). Blood leukocyte counts were performed every 0.25 hours from 0 to one hour and then every one hour. Differential counts were done on Wright stained smears in duplicate. Peripheral circulating neutrophil number was obtained by multiplying absolute white blood cell count times the percent of segmented neutrophils plus the percent of banded neutrophils. Thermal dilution cardiac output measurements were performed every 0.25 hour from 0 to one hour and then every one hour. Three ml of normal saline cooled to 0° C. were injected into the proximal port of the Swan-Ganz catheter and the mean of three consecutive cardiac output measurements initiated at end-exhalation was calculated.

BACTERIAL COUNTS IN BLOOD

At 2.5 hours a 2 ml blood sample was withdrawn from the femoral arterial line. Samples were obtained from 2 animals in Group I, 3 animals from group II, and 3 animals from Group III. The vial contained sterile heparin and was immediately processed to determine the number of CFU in the blood. An aliquot was lysed in sterile water and calibrated loops were used to innoculate MacConkey, blood, and trypicose soy agar plates. The plates were incubated at 37° C. overnight and read the next day for growth. Positive cultures were gram-stained, assessed for hemolysin, and assessed for slide agglutination using anti-J96 0 antigen serum as described elsewhere (O'Hanley, et al. (1985), "Molecular basis of *Escherichia coli* colonization of the upper tract in Balb/C mice." J. Clin. Invest., in press). Normal rabbit anti-sera was used as a negative control in the slide agglutination assay.

GRAVIMETRIC ANALYSIS

At the completion of the 4 hour experimental protocol (or at death) 10,000 units of sodium heparin was injected into a central venous line. After 5 minutes, 250 meq of potassium chloride was injected intravenously and the endotracheal tube clamped. At death a median sternotomy was performed. The lung hila were clamped and the lungs excised. Gravimetric analysis was done using the method described in detail by Mihm, et al. (1982), "Measurement of extravascular lung water in dogs using the thermal-green dye dilution method." Anesthesiology 57, 116–122. Extravascular lung water (EVLW) was calculated and reported as ml per kg body weight.

STATISTICS

Comparisons were made between groups using the nonparametric Wilcoxon-signed rant test (Snedecor, G. W. and W. G. Cochran (1980), "Stastical methods." Iowa State University Press, Ames, IO, Seventh Ed., 144–146). $P<0.05$ was considered significant. All values in tables, figures or text are mean values±standard deviation.

The results of the foregoing study are summarized below.

LEUKOCYTE AGGREGATION

Endotoxin activated plasma (EAP) alone or EAP plus nonspecific rabbit IgG served as a potent stimulus for leukocyte aggregation. When EAP was incubated with anti-C5a antibody the leukocyte aggregating potential of the stimulus was abolished.

PRIMATE SURVIVAL AND HEMODYAMIC DATA

The intravenous infusion of $1 \times 10^{10}$ *E. coli*/kg proved to be lethal in 3 of 4 animals in Group II. Group II animals died at 105, 150, and 180 minutes from cardiac arrhythmias and cardiovascular collapse. The animals that died at 150 and 180 minutes also had florid pulmonary edema seen in the endotracheal tube. The fourth animal in Group II survived the experimental protocol and had a MAP of 35 mmHg at 4 hours (Table I). In contrast all control animals (Group I) and all animals treated with anti-C5a antibodies (Group III) survived for 4 hours and were then sacrificed.

All primates receiving *E. coli* developed septic shock manifested by hypotension, tachycardia, and decreased systemic vascular resistance (SVR) (Table I). All group III primates survived and had a significant recovery in their MAP beginning at 105 minutes ($p<0.05$). There are no significant difference between groups I, II, and III in mean PAP, PCWP or cardiac output.

Septic primates in Group II had significantly greater net fluid intake, 52±17 ml/kg/hr than Group I, 9±8 ml/kg/hr or Group III, 23±11 ml/kg/hr. There was no significant difference in net fluid intake between Groups I and III.

PULMONARY INJURY

Pulmonary injury was assessed by analyzing $AaDO_2$ and EVLW. Baseline $AaDO_2$ results were not significantly different between Groups I, II, and III. $AaDO_2$ results calculated near death from arterial blood gases were significantly increased in Group II animals, 65±29 mmHg ($p<0.05$) as compared to control (Group I) primates, 23±6.5 mmHg, or anti-C5a antibody (Group III) treated primates, 20±10 mmHg.

EVLW results demonstrated significantly increased lung water ($p<0.05$) in the septic primates (Group II), 5.0±1.1 ml/kg, as compared to controls, 1.7±0.3 ml/kg or anti-C5a antibody treated primates, 2.6±0.4 ml/kg. There was no significant difference in EVLW between Groups I and III.

PERIPHERAL CIRCULATING NEUTROPHILS

Peripheral neutrophil counts revealed a significant ($p<0.05$) and sustained neutropenia in Groups II and III animals when compared to Group I (Table I). There was no difference in circulating peripheral neutrophil count between animals in Groups II and III.

BACTERIAL COUNTS IN BLOOD

Bacterial growth from blood obtained at 2.5 hours was not detected on any of the plates incubated with samples obtained from Group I monkeys. In contrast, $1.0–4.5 \times 10^4$ CFU/ml of blood was detected in Groups II and III animals. All cultures revealed gram negative organisms that had uniform colony morphology on the plates, uniform and hemolytic colonies on blood agar and uniform positive lactose fermenting colonies on MacConkey agar. Furthermore, the colonies were agglutinated only by anti-96 0 antisera. From these data, it is evident that all moneys administered intravenous *E. coli* J 96 had a pure bacteremia due to this organism.

TABLE I

| | Effects of Anti-C5a Antibodies on Hemodynamics in Septic Primates | | |
|---|---|---|---|
| | CONTROL (Group I) | SEPTIC (Group II) | SEPTIC + ANTI-C5a ANTIBODIES (Group III) |
| Weight | 5.7 ± 0.8 kg* | 5.9 ± 1.0 | 5.5 ± 0.3 |
| Survival | 4/4 | 1/4 | 4/4 |
| Peripheral Circulating Neutrophils at 15 min** (cells/mm³) | 13.0 ± 2.7*** | 1.5 ± 0.9 | 1.5 ± 0.6 |
| MAP (mmHg) | 108 ± 15*** | 60 ± 9 | 64 ± 8 |
| MAP at 105 min (mmHg) | 107 ± 17**** | 36 ± 18**** | 64 ± 12**** |
| Heart Rate (beats/min) | 170 ± 13*** | 200 ± 7 | 208 ± 21 |
| PCWP (mmHg) | 3 ± 1 | 4 ± 1 | 3 ± 2 |
| Cardiac Output (L/min) | 1.2 ± 0.2 | 1.5 ± 0.5 | 1.5 ± 0.3 |
| SVR (dyne-sec/cm⁵) | 7037 ± 1624*** | 3349 ± 1203 | 3370 ± 848 |
| PAP mean at 0 min (mmHg) | 14 ± 3 | 19 ± 4 | 16 ± 3 |

*Mean ± SD
**All values are obtained at 60 minutes except where noted
***Values significantly different ($p < 0.05$) from Groups II and III
****All values significantly different ($p < 0.05$) from each other

We claim:

1. A method for treating adult respiratory distress syndrome (ARDS) in a subject in need thereof which comprises administering to said subject an antibody to complement component C5a or the des Arg derivative thereof in an amount effective to treat ARDS.

2. A method of claim 1 wherein the amount of antibody administered attenuates ARDS.

3. A method of claim 1 wherein the antibody is a polyclonal antibody.

4. A method of claim 1 wherein the antibody is anti-human C5a or anti-human C5a des Arg.

5. A method of claim 1 wherein the amount of antibody administered on a per diem basis is 1 to 100 mg/kg of subject weight.

6. A method of treating sepsis in a subject in need thereof which comprises administering to said subject an antibody to complement component C5a or the des Arg derivative thereof in an amount effective to treat sepsis.

7. The method of claim 6 wherein the amount of antibody administered on a per diem basis is 1 to 100 mg/kg of subject weight.

8. The method of claim 1 wherein the subject is a human.

* * * * *